United States Patent [19]
Oehy et al.

[11] Patent Number: 5,645,606
[45] Date of Patent: Jul. 8, 1997

[54] OUTER SHELL FOR AN AT LEAST TWO-SHELL JOINT SOCKET OF A HIP JOINT PROSTHESIS

[75] Inventors: Jürg Oehy; Kurt Bider, both of Winterthur; Martin Schoch, Stallikon, all of Switzerland

[73] Assignee: Sulzer Medizinaltechnik AG, Winterthur, Switzerland

[21] Appl. No.: 372,416

[22] Filed: Jan. 13, 1995

[30] Foreign Application Priority Data

Feb. 7, 1994 [EP] European Pat. Off. ............ 94810065

[51] Int. Cl.$^6$ .................................................... A61F 2/32
[52] U.S. Cl. ............................................. 623/22; 623/18
[58] Field of Search .................................. 623/16, 18, 19, 623/20, 22, 23; 606/62–71

[56] References Cited

U.S. PATENT DOCUMENTS

| | | | |
|---|---|---|---|
| 4,388,921 | 6/1983 | Sutter et al. | 606/71 |
| 4,484,570 | 11/1984 | Sutter et al. | 606/71 |
| 4,653,487 | 3/1987 | Maale | 606/62 |
| 4,955,325 | 9/1990 | Zarnowski . | |
| 5,074,879 | 12/1991 | Pappas et al. | 623/23 |
| 5,246,459 | 9/1993 | Elias | 623/20 |
| 5,330,535 | 7/1994 | Moser et al. | 623/20 |

FOREIGN PATENT DOCUMENTS

| | | |
|---|---|---|
| 0420795 | 4/1991 | European Pat. Off. . |
| 0444381 | 9/1991 | European Pat. Off. . |
| 0490616 | 6/1992 | European Pat. Off. . |
| 0500477 | 8/1992 | European Pat. Off. . |
| 2592787 | 7/1987 | France . |
| 674927 | 8/1990 | Switzerland . |

*Primary Examiner*—David Isabella
*Attorney, Agent, or Firm*—Townsend and Townsend and Crew LLP; J Georg Seka; John T. Raffle

[57] ABSTRACT

The outer shell (5) comprises a plurality of through-holes (12) which are provided for the receipt of fastening elements (14) for the fastening of the outer shell (5) in a bone seat (4) and which are each provided with an inner counter-sink (25). The through-holes (12) which are free of fastening elements (14) are each provided with a sealing plug (15) which is insertable from the inside outwards and designed with a sealing surface supportable in and extending around the counter-sink (25). The sealing plug (15) comprises a number of spiral springs (18) which are insertable into the relevant through-hole (12) and form a snap connection with the wall of the through-hole (12), as well as a hat-like central projection (17) disposed separated from the spiral springs (18) which is provided with an inwardly open blind bore (17a) for the receipt of a placement tool (20) screwable into it. A reliable sealing off of the through-holes (12) is thus achieved and escape into the bone seat 4 of any rubbed-off particles produced within the outer shell 5 is prevented.

8 Claims, 1 Drawing Sheet

OUTER SHELL FOR AN AT LEAST TWO-SHELL JOINT SOCKET OF A HIP JOINT PROSTHESIS

BACKGROUND OF THE INVENTION

The invention relates to an outer shell for an at least two-shell joint socket of a hip joint prosthesis, wherein the outer shell comprises a plurality of through-holes which are designed for the receipt of fastening elements for the fastening of the outer shell in a bone seat and which are each implemented with a counter-sink formed on the inner side of the outer shell.

The invention further relates to a hip joint prosthesis implemented with an outer shell of this kind and also to closure plug of an outer shell of this kind.

A joint socket of the named kind is described in CH-PS 674 927 and comprises a metallic outer shell and a plastic inner shell fittable therein, the socket is provided with a metallic dividing layer in the region of the through-holes which perforate the outer shell, this layer being in the form of a shell body formed from a metal sheet and fitted into the outer surface of the inner shell. Creep or cold flow of the plastic of the inner shell into those through-holes of the outer shell which remain free of fastening elements is intended to be prevented by this dividing layer to avoid direct contact between the bone tissue and rubbed-off plastic which may occur in the region of these through-holes. The relatively complicated three-part construction of the known joint socket requires stocking of a corresponding number of different shell bodies for the construction of the corresponding dividing layers, this is especially so for embodiments in which a supply of outer and inner shells with various grades of sizes are stocked.

SUMMARY OF THE INVENTION

The object of the invention is to provide, especially in this respect, an improved, simplified embodiment of a joint socket which provides a screening of the bone tissue from undesired contact with particles rubbed off by wear and which is independent of the design of the inner shell and from the corresponding size of the outer shell.

The present invention is directed to an outer shell for a two-shell joint socket of a hip joint prosthesis. The outer shell comprises a plurality of through-holes extending through the shell body and being adapted to receive fastening elements for fastening the shell body into a bone seat. One or more closure plugs are inserted into through-holes that do not receive fastening elements from the inner sides of the shell body. The closure plugs each have a sealing surface supported in and extending around a countersink of the corresponding through-hole. Closure plugs further include a plurality of flexible springs inserted into the corresponding through-hole and protruding from the sealing surface towards the outer side of the shell body to form a snap connection between the closure plug and the corresponding through-hole.

Fitting the outer shell of the invention with a plurality of closure plugs allows a desired and individually controllable local screening prior to the fitting of the inner shell of each and every one of the portions of bone tissue situated in the region of these through-holes from the inner volume of the outer shell. The closure plugs designed in accordance with the invention are relatively easy to manufacture and can be made available to the surgeon in relatively large supplies and may be placed into or removed from the relevant through-holes by the surgeon in a simple manner. The embodiment of the invention allows an independent sealing off of through-holes, in particular independent of the form and the mounting of the inner shell, at an advantageously early phase of the operation, for instance prior or directly subsequent to fitting the outer shell into the bone seat. The outer shell fitted in accordance with the invention further allows the use of an advantageously simple design of inner shell in a shape which is completely independent of the arrangement of the closure plugs.

The invention is described with the aid of an embodiment which is schematically illustrated in the drawing. They show:

DESCRIPTION OF THE PREFERRED EMBODIMENTS

Figure 1:
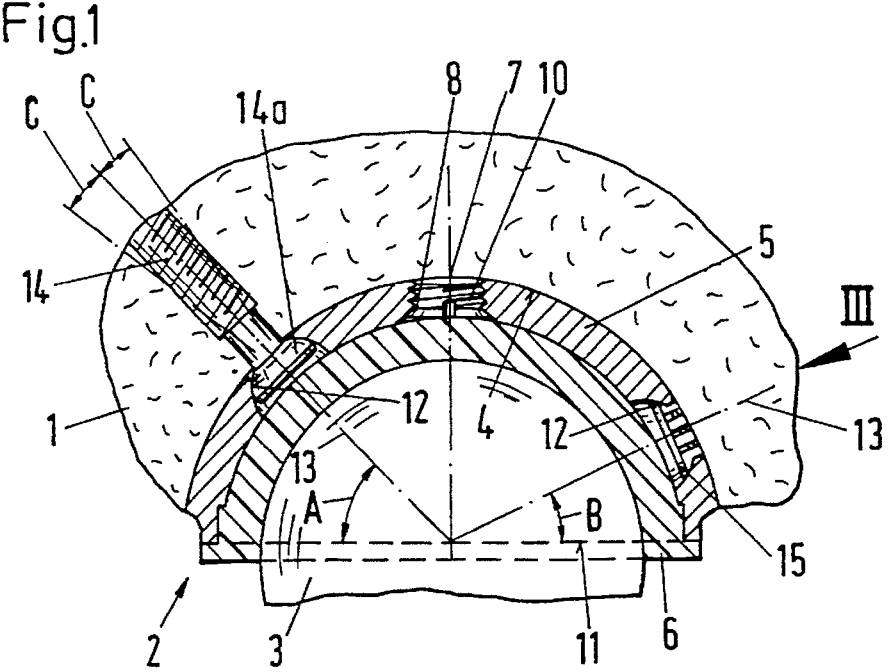
FIG. 1 illustrates a hip joint prosthesis designed in accordance with the invention comprising a joint socket and in a diametrically extending section.
Figure 2:
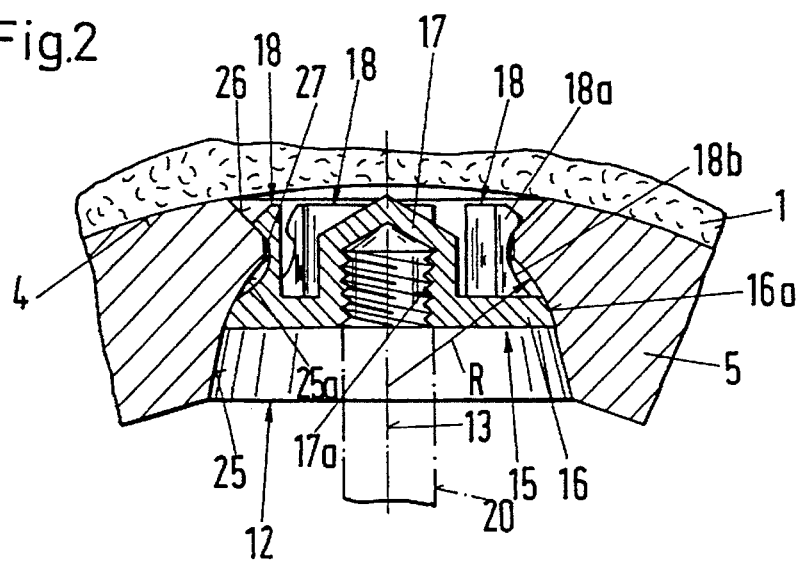
FIG. 2 is an enlarged view of the joint socket of FIG. 1 with a closure plug in a section corresponding to the line II—II in FIG. 3.
Figure 3:
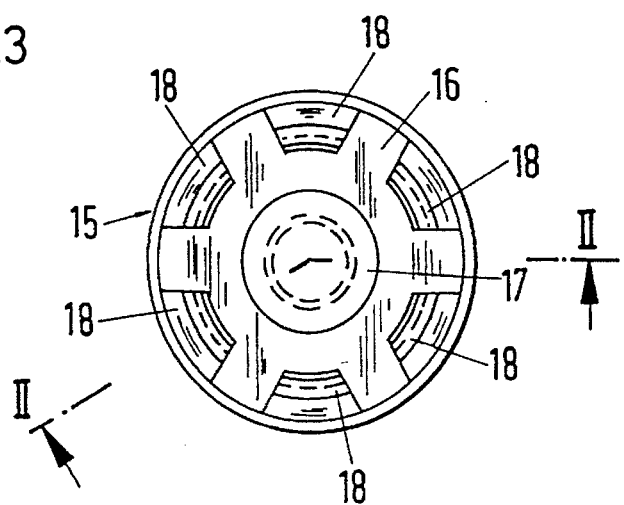
FIG. 3 the closure plug of FIG. 2 in a plan view in accordance with arrow III in FIG. 1.

The hip joint prosthesis of FIGS. 1 and 2 comprises a joint socket 2 which is fittable into the bone tissue 1 of a human pelvis and a joint head 3 which is fastenable in a femur via a shank part which is not illustrated. The joint socket 2 comprises a metallic outer shell 5, for instance made from titanium, which is insertable into and anchorable in a prepared bone seat 4 and which is substantially in the form of a hollow hemi-sphere and a matched inner shell 6 which can be fitted therein and which is also hemi-spherical and which receives the joint head 3 and which, in accordance with the illustration, is made from a plastic such as polyethylene. In accordance with another embodiment, a corresponding metallic inner shell can also be provided. In accordance with a further embodiment which is not illustrated, there may also be provided an intermediate shell between the outer shell 5 and the inner shell 6, wherein the intermediate shell can be made from a plastic or a metal.

In the region of its pole 7, the outer shell is provided with a threaded bore 8 which is designed for the receipt of a sealing element 10 which can be screwed into it from the inside outward, this sealing element 10 not being subject matter of the current invention. Further radial through-holes 12 which are displaced relative to one another in the circumferential direction are provided between the pole 7 and the equator 11 of the outer shell 5 these through-holes 12 perforate the outer shell 5 with axes 13 inclined at various angles 'A' and 'B' relative to the plane of the equator. Each of the through-holes 12 is provided for the receipt of a fastening element 14 of any kind which is anchorable in the bone tissue 1 and which, in accordance with the illustration, is in the form of a bone screw screwable into the bone tissue 1. Two or more, for instance 3 corresponding fastening elements 14 can also be provided for the fastening of the outer shell 5 in the bone seat 4. The through-holes 12 of the outer shell 6 which have not been used and which are free of fastening elements 14 are provided with closure plugs 15 which are fittable and fastenable from the inside outwards, only one of them being illustrated in FIG. 1.

Corresponding to the illustration of FIGS. 1 and 2, the through-holes 12 are each designed with an inner countersink 25 and an outer counter-sink 26 which together with the inner counter-sink 25 defines a locally narrowed circumferential part 27 of the through-hole 12. As can be seen in particular from FIG. 2, the inner counter-sinks 25 of the through-holes 12 can each have a dome-like shape determined by a conically shaped inner end portion and an approximately spherical support surface 25a formed between the end portion and the circumferential part 27. In accordance with FIG. 2, the support surfaces 25a are each formed with a radius 'R'. In accordance with FIG. 1, the fastening elements 14 can each be designed with a head part 14a which has a corresponding convex butting surface which is thus seatable onto the concave support surface 25a and which, dependent on the mounting of the fastening element 14 in the bone tissue 1, in each case permits an angular positioning which corresponds to that of the axis 13 of the through-hole 12 or one which deviates from this axis 13 by an angle 'C' indicated in FIG. 1. The embodiment illustrated thus allows a corresponding mounting which is variable within this angular range to the particular anatomical conditions prevailing.

The closure plugs 15 each comprise a plate-like sealing part 16 which is insertable flush into the inner counter-sink 25 of those through-holes 12 which are not utilized, a central hat-like projection 17 protruding from the sealing part 16 towards the outer side of the outer shell 5, and a number of flexible springs 18 (six in the embodiment) arranged segmentally protruding from an edge portion of the sealing part 16 towards the outer side of the outer shell 5. The sealing part 16 is formed with a sealing surface 16a extending around the circumference of the sealing part 16 and seatable onto a wall portion of the counter-sink 25, in the embodiment onto the support surface 25a. The closure plug 15 is held in the through-hole 12 via the flexible springs 18 and pressed onto the support surface 25a with the sealing surface 16a. As can be seen, in particular from FIG. 2, the sealing surface 16a can be formed by a counter surface of the sealing part 16 which is spherical corresponding to the support surface 25a and which cooperates with the support surface 25a via a ring-shaped contact surface and thus effects an effective sealing off of the through-hole 12. The projection 17 is formed with a blind bore 17a which is open towards the inner side of the outer shell. The blind hose 17a, in accordance with the embodiment, can be provided with a thread and which is designed for the receipt of a driver part of a placement tool 20 which is illustrated by dot dashed lines. The flexible springs 18 are formed by elastically deformable finger-like wall segments which extend outwardly from the edge region of the sealing part 16 and which are moveable relative to one another and which each have an end portion 18a insertable into the outer counter-sink 26 and tensable against its wall, and a groove-like recess 18b corresponding to the narrowed circumferential part 27 of the through-hole 12 and for the receipt of this part.

The closure plugs 15, which can be made from the same material as the outer shell 5, e.g., a titanium alloy, can each be inserted into the through-hole 12 by the placement tool 20, wherein the flexible springs 18 are deformed when the end part 18a passes over the circumferential part 27 and subsequently form a snap connection with the wall of the through-hole 12 via which the sealing part 16 is tensioned with the sealing surface 16a towards the support surface 18a. In addition, the part of the bone tissue 1 located in the region of the through-hole 12 is sealed off from the inner side of the outer shell 5, thereby preventing the escape of particles rubbed off by wear. The closure plugs 15 can be placed into and removed from the through-holes 12 in a simple manner via the placement tool 20. The embodiment of the closure plugs 15 described makes possible a reliable sealing off of the through-holes 12 even for relatively thin outer shells 5, for instance ones with wall thicknesses of 4 to 5 mm, which, as a rule, are not suited for the application of threads.

Numerous derivative embodiments of the invention are possible. For example, the sealing part 16 can also be designed with a differently formed sealing surface 16a, for instance a cylindrical or conical one, which can be provided for cooperation with the support surface 25a or with the conical end section 25 of the counter-sink. In accordance with an embodiment which is not illustrated, the inner counter-sinks of the through-holes 12 can each be made conical over the entire depth and be provided for the receipt of a correspondingly conical head part of a fastening element or—as is known from the above-mentioned CH-PS-674 927—from a conical sheath which can receive a fastening element mountable in various angular positions. The closure plugs 15 can, also in this embodiment, be designed with conical sealing surfaces which are areally seatable onto the counter-sinks 25 optionally with for instance cylindrical sealing surfaces which are contactable with linear contact. In place of the illustrated screw connection, a different driving connection could also be provided between the projection 17 and the placement tool 20, for instance a releasable hook connection or similar. It is to be further understood that in any embodiment each of the closure plugs can also be provided with a number of flexible springs 18 which deviates from the arrangement illustrated, for instance three, four, eight or more.

In summary, the invention can be described as follows:

The outer shell 5 comprises a plurality of through-holes 12 which are provided for the receipt of fastening elements 14 for the fastening of the outer shell 5 in a bone seat 4 and which are each formed with an inner counter-sink 25. The through-holes 12 which are free of fastening elements 14 are each provided with a closure plug 15 which can be fitted in from the inside outwards and which is formed together with a sealing surface 16a supportable in and extending around the counter-sink 25. The closure plug 15 comprises a number of flexible springs 18 which are insertable into the relevant through-hole 12 and which form a snap connection with the wall of the through-hole 18 and further comprises a hat-like central projection 17 which is disposed at a distance apart from the flexible springs 18 and which is provided with a blind bore 17a open toward the inside for the receipt of a placement tool 20 screwable into the blind bore 17a. A reliable sealing off of the through-holes 12 is thus achieved and escape into the bone seat 4 of any rubbed-off particles produced within the outer shell 5 is prevented.

We claim:

1. An outer shell for a joint socket of a hip joint prosthesis comprising:

a shell body having inner and outer sides and a thickness therebetween, the shell body defining a plurality of through-holes extending from the inner to outer sides and being adapted to receive fastening elements for fastening the shell body in a bone seat, the through-holes each including a countersink facing the inner side of the shell body; and at least one closure plugs inserted into at least one of the through-holes from the inner sides of the shell body, the closure plugs each having a sealing surface supported in and extending around the countersink of the corresponding through-hole, the closure plugs each including a plurality of flexible springs inserted into the corresponding through-hole and protruding from the sealing surface towards the outer side of the shell body to form a snap connection between the closure plug and the corresponding through-hole, the closure plugs having a length less than or equal to the thickness of the shell body.

2. The outer shell of claim 1 wherein the countersinks of the through-holes each have a dome shape defined by a substantially spherical support surface, the closure plugs each being defining a spherical edge portion seated on a corresponding spherical support surface.

3. The outer shell of claim 1 wherein the closure plugs each comprise a central projection spaced from the flexible springs and protruding towards the outer side of the outer shell, the central projections each defining an inner bore opening inwardly for receiving a driver part of a placement tool.

4. The outer shell of claim 3 wherein the bore is provided with a thread.

5. The outer shell of claim 1 wherein the flexible springs comprise individually movable finger-like wall segments of the closure plug.

6. The outer shell of claim 3 wherein the through-holes further define an outer countersink formed adjacent the outer side of the outer shell, the inner and outer countersinks defining a locally narrowed circumferential part therebetween, wherein the flexible springs each include an end portion inserted into the outer countersink and a groove corresponding to the narrowed circumferential part.

7. A hip joint prosthesis comprising:

an inner shell adapted for receiving a joint head; and an outer shell comprising:

a shell body having inner and outer sides and a plurality of through-holes extending therethrough and being adapted to receive fastening elements for fastening the shell body in a bone seat, the shell body having a thickness from the inner to outer sides and the through-holes each including a countersink facing the inner side; and at least one closure plugs inserted into at least one of the through-holes from the inner sides of the shell body, the closure plugs each having a sealing surface supported in and extending around the countersink of the corresponding through-hole, the closure plugs each including a plurality of flexible springs inserted into the corresponding through-hole and protruding from the sealing surface towards the outer side of the shell body to form a snap connection between the closure plug and the corresponding through-hole, the closure plugs having a length less than or equal to the thickness of the shell body.

8. An outer shell for a joint socket of a hip joint prosthesis comprising:

a shell body having inner and outer sides and a plurality of through-holes extending therethrough and being adapted to receive fastening elements for fastening the shell body in a bone seat, the shell body having a thickness from the inner to outer sides and the through-holes each including a countersink facing the inner side; and one or more closure plugs inserted into one or more of the through-holes from the inner sides of the shell body, the closure plugs each having a sealing surface supported in and extending around the countersink of the corresponding through-hole, the closure plugs each including a plurality of flexible springs inserted into the corresponding through-hole and protruding from the sealing surface towards the outer side of the shell body to form a snap connection between the closure plug and the corresponding through-hole, the closure plugs having a length less than or equal to the thickness of the shell body, the closure plugs each comprising a central projection spaced from the flexible springs and protruding towards the outer side of the outer shell, the central projections each defining an inner bore opening inwardly for receiving a driver part of a placement tool.

* * * * *

UNITED STATES PATENT AND TRADEMARK OFFICE
Certificate

Patent No. 5,645,606                                                                        Patented: July 8, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Jürg Oehy, Winterthur, Switzerland; Kurt Bider, Winterthur, Switzerland; Martin Schoch, Stallikon, Switzerland; Nikolaus Böhler, Linz, Austria; and Wolfgang Schwägerl, Wien, Austria.

Signed and Sealed this Twenty-seventh Day of August 2002.

CORRINE M. MCDERMOTT
*Supervisory Patent Examiner*
Art Unit 2835

UNITED STATES PATENT AND TRADEMARK OFFICE
Certificate

Patent No. 5,645,606                                           Patented: July 8, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Jürg Oehy, Winterthur, Switzerland; Kurt Bider, Winterthur, Switzerland; Martin Schoch, Stallikon, Switzerland; Nikolaus Böhler, Linz, Austria; and Wolfgang Schwägerl, Wien, Austria.

Signed and Sealed this Nineteenth Day of November 2002.

CORRINE M. MCDERMOTT
*Supervisory Patent Examiner*
Art Unit 3738